(12) United States Patent
Kirihara et al.

(10) Patent No.: US 6,599,470 B1
(45) Date of Patent: Jul. 29, 2003

(54) PROCESS AND DEVICE FOR COUNTERACTING AND DEODORIZING FORMALIN GAS

(75) Inventors: Chikao Kirihara, Kyoto (JP); Takanori Ono, Kyoto (JP); Mamoru Nogami, Kyoto (JP)

(73) Assignee: Mediate Co., Ltd., Kyoto (JP)

( * ) Notice: Subject to any disclaimer, the term of this patent is extended or adjusted under 35 U.S.C. 154(b) by 0 days.

(21) Appl. No.: 09/555,326
(22) PCT Filed: Jun. 3, 1999
(86) PCT No.: PCT/JP99/02984
§ 371 (c)(1), (2), (4) Date: May 24, 2000
(87) PCT Pub. No.: WO00/18495
PCT Pub. Date: Apr. 6, 2000

(30) Foreign Application Priority Data

Sep. 25, 1998 (JP) .............................................. 10-288721

(51) Int. Cl.[7] .................................................. A61L 2/00
(52) U.S. Cl. ................... 422/2; 422/4; 422/5; 422/168; 422/306
(58) Field of Search ........................... 422/2, 4, 5, 168, 422/306

(56) References Cited

U.S. PATENT DOCUMENTS

| | | | |
|---|---|---|---|
| 5,120,512 A | * | 6/1992 | Masuda ...................... 422/198 |
| 5,229,071 A | * | 7/1993 | Meo, III ...................... 422/126 |
| 5,283,035 A | * | 2/1994 | Karthaus et al. .............. 422/28 |

FOREIGN PATENT DOCUMENTS

| | | |
|---|---|---|
| JP | 59-190248 (U) A | 12/1984 |
| JP | H8-57027 | 3/1996 |

* cited by examiner

Primary Examiner—Krisanne Thornton
(74) Attorney, Agent, or Firm—Koda & Androlia

(57) ABSTRACT

A formalin gas counteracting and deodorizing device which is connected to a sterilization chamber including a main pipeline having an inlet for formalin gas at one end thereof and an outlet for processed gas at the other end, a fan connected to the inlet side midway in the main pipeline, an oxidation means for decomposition, a cooling means all connected in this order from the fan to the outlet, and a branch pipe provided between the oxidation means of the main pipeline and the cooling means. The process includes performing sterilization utilizing the sterilizer for a predetermined period of time, circulating the gas between the main pipeline, and the bypass pipe line for a predetermined period of time using the formalin gas counteracting and deodorizing device just before the end of the sterilization process, then circulating the gas between the sterilization chamber and the main pipeline for counteracting the formalin gas and introducing a counteractive into the sterilization chamber.

6 Claims, 3 Drawing Sheets

PROCESS AND DEVICE FOR COUNTERACTING AND DEODORIZING FORMALIN GAS

The present invention relates to a process and device for counteracting and deodorizing formalin gas.

BACKGROUND TECHNIQUE

Today, the sterilization processes adopted in the medical facilities are those as based on the use of high-pressure steam sterilizers, gas sterilizers, or ultraviolet sterilizers for articles being disinfected, and, above all, the formalin sterilizer is used the mostly on the grounds that it is economical on liquid medicine, and in addition it has a strong sterilizing power. And among others, the system using ammonia gas is generally used as a neutralization or counteraction method for formaldehyde gas yielding from formalin gas, but with such a system, a complete counteraction is difficult.

Therefore, the fact is that formaldehyde gas, ammonia gas, etc., in an uncompleted state of counteraction are discharged from the sterilization chamber to the outside through the exhaust duct (for instance, Japan Patent Kokai 1996-057027).

It is true that the formalin sterilization has many advantages with it, but it has nevertheless a big disadvantage. Formalin has a peculiar strong stimulative smell, and if such a smell remains as residual gas in articles being sterilized, sterilization workers or inpatients may be exposed to the formaldehyde gas, which may be a great obstacle to health. The discharge of such a gas to the atmosphere will pose a real threat to the perimeter in terms of environmental preservation.

The object of the present invention is to solve the above subjects and to provide a process and a device for a formalin gas counteracting and deodorizing which may prevent formalin smell from remaining in those things without resort to evacuation after sterilization by means of its compact equipment.

DISCLOSURE OF THE INVENTION

For solution of said subjects, the process and device of the present invention has been developed. Said device is a circulation-typed formalin gas purifying device wherein rather than being discharged outside after sterilized, a formaldehyde gas with which the sterilization chamber is filled is introduced into the counteracting and deodorizing device for purification.

Moreover, the process and device may mark a new epoch in this field and greatly contribute to the environmental preservation in that formaldehyde gas etc., may be removed completely, and upon controlling the temperature and humidity in the chamber, sterilized articles may be taken out.

A process in the first construction comprises connecting to the sterilization chamber a formalin gas counteracting and deodorizing device which includes a main pipeline having an inlet for formalin gas at one end thereof and an outlet for processed gas at the outer; a fan connected to said inlet side midway in said main pipeline; a preheater means; a decomposition by oxidization means; and a cooling means all ranging in this order from said fan to said outlet to connect to each other; and a bypass pipeline provided to cover a section extending from the fan of said main pipeline to the cooling means, circulating the gas for idling between said main pipeline and said bypass pipeline for a predetermined period of time by said formalin gas counteracting and deodorizing device just before the end of said sterilization process, and then administering the same treatment as done in said formalin gas.

A process in the second construction comprises connecting to the sterilization chamber a formalin gas counteracting and deodorizing device which includes a main pipeline having an inlet for formalin gas at one end thereof and an outlet for processed gas at the other; a fan connected to said inlet side midway in said main pipeline; a preheater; a decomposition by oxidization means; a cooling means all ranging in this order from said fan to said outlet to connect to each other; and a branch pipe provided between the decomposition by oxidization means of said main pipeline and the cooling means, performing sterilization by the use of said sterilizer for a predetermined period of time, circulating the gas for idling between said pipeline, said branch pipe and said sterilization chamber for a predetermined period of time by the use of said formalin gas counteracting and deodorizing device after the end of said sterilization course, then circulating the gas between the sterilization chamber and the main pipeline for counteraction purpose with said branch pipe stopped up, then introducing a counteractive into the sterilization chamber, and making the same treatment as done in the case of said formalin gas.

A device in the third construction includes a main pipeline having an inlet for formalin gas at one end thereof and an outlet for processed gas at the other, a fan connected to said inlet side midway in said main pipeline, a preheater, a decomposition by oxidization means, and a cooling means all ranging in this order from said fan to said outlet to connect to each other, and a bypass pipeline provided to cover a section extending from the fan of said main pipeline to the cooling means.

A device in the fourth construction includes a main pipeline having an inlet for formalin gas at one end thereof and an outlet for processed gas at the other, a fan connected to said inlet side midway in said main pipeline, a preheater, a decomposition by oxidization means, and a cooling means all ranging in this order from said fan to said outlet to connect to each other, and a branch pipe provided between the decomposition by oxidization means of said main pipeline and the cooling means.

In a device in the fifth construction, in addition to any one of above constructions, said cooling means includes a case having an inlet and outlet for processed gas, a cooling coil contained in said case, a metallic tube connected to said outlet while remaining in contact with said coil so as to direct the processed gas at the outlet.

In a device in the sixth construction, in addition to the third, fourth or fifth structure, the sterilization chamber is connected to said inlet and outlet for processed gas.

The present invention is in no need of exhaust duct because neither gas nor air in the chamber is discharged outside (no need to evacuate gas or air). Even if a high-temperature sterilization took place, the temperature within the sterilization chamber can be lowered to a normal temperature by strong actions of the cooling device and dehumidifying device attached to the system to ensure that the chamber door is opened without danger.

Since the circulation of gas through the bypass pipeline or branch pipe may give to the gas a chance to be heated to such a degree that the latter may keep stable, the undestroyed gas invasion into the cooling means, which may result in dissolution of a harmful gas in the condensation, can be prevented.

The device in accordance with the present invention is a high-performance device wherein as not only formaldehyde gas but also ammonia gas and other gases can be simply and completely counteracted and deodorized, so that the device may be also applied to different fields besides for the medical organs. On top of that, the temperature at the sterilization chamber's side can be controlled, and the humidity can be reduced by the dehumidifying/cooling apparatus, whereby the device may be used to precision medical appliances, beds, mattresses, linens, and other articles being sterilized, and also compatible with other maker's sterilizers.

THE MOST PREFERRED EMBODIMENT EMBODYING THE INVENTION

Figure 1:
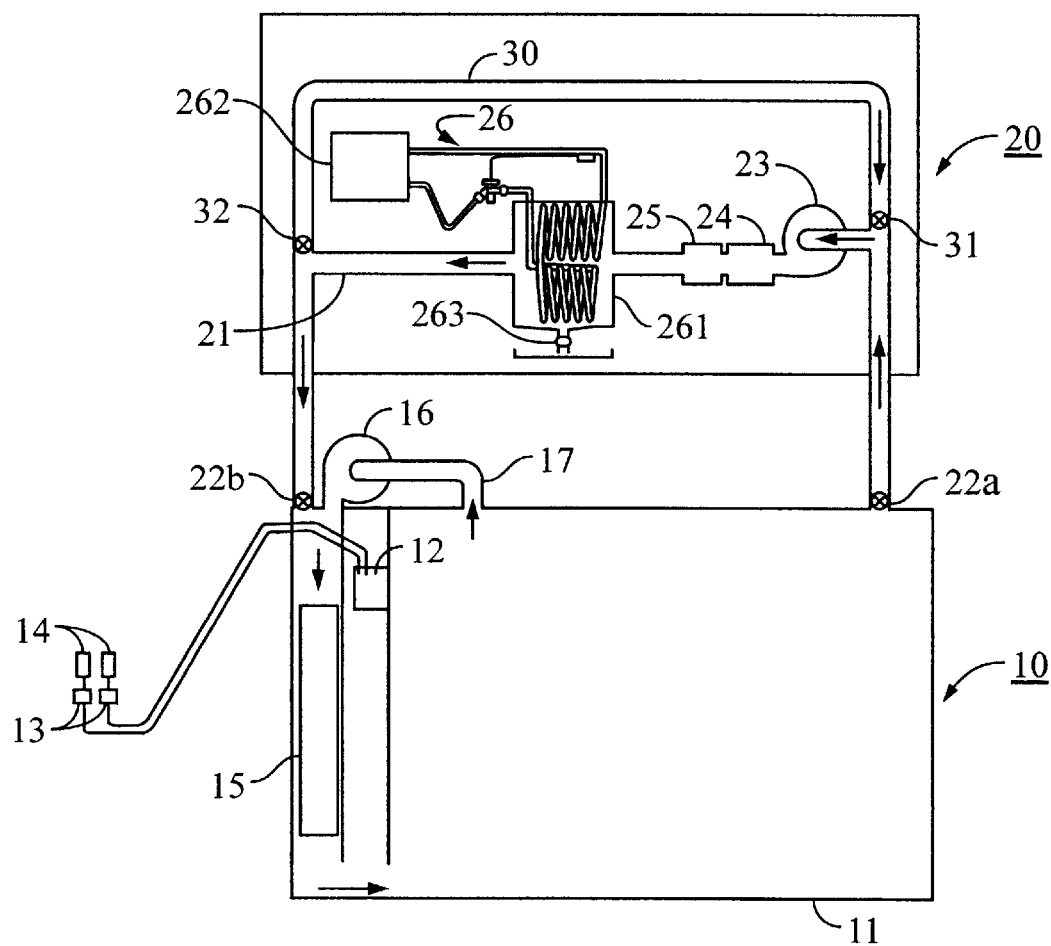
FIG. 1 is a system diagram of one embodiment of the present invention.

The embodiment of the present invention will be described with reference to one example as shown in the drawing.

Referring to FIG. 1, a formalin gas counteracting and deodorizing device 20 is connected with as sterilizer 10 in order to put a formalin gas prepared in the sterilizer 10 upon chemical treatment to make it innocuous. The sterilizer 10 has a liquid medicine vaporizing apparatus 12 disposed in a sterilization chamber 11, with which an outside pump 13 and a liquid medicine tank 14 communicate. There are provided a heater 15 for warming the interior of the chamber in the sterilizing chamber 11, and a fan 16 for warming the interior of the chamber 11 placed midway in a duct 17.

Said formalin gas counteracting and deodorizing device 20 comprises a main pipeline 21 having an inlet for formalin gas at one end thereof and an outlet for processed gas at the other; a decomposition fan 23 connected to said inlet's side midway in said main pipeline; and a preheating means 24, decomposition by oxidization means 25 consisting of catalyst, and a dehumidifying/cooling apparatus 26, all ranging in this order from said fan to said outlet's side to connect to each other. The main pipeline 21 is connected to said sterilizer 10 through a suction valve 22a and a discharge valve 22b. A bypass pipeline 30 is connected to a section provided to extend from the fan 23 to the cooling means 26 through a first selector valve 31 and a second sector valve 32.

Figure 3:
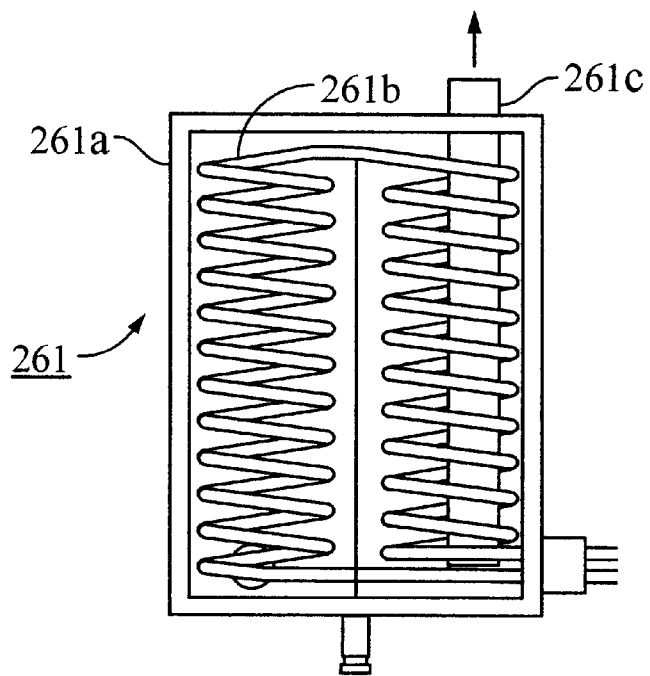
FIG. 3 is a sectional front view of a dehumidifying/cooling apparatus.
Figure 4:
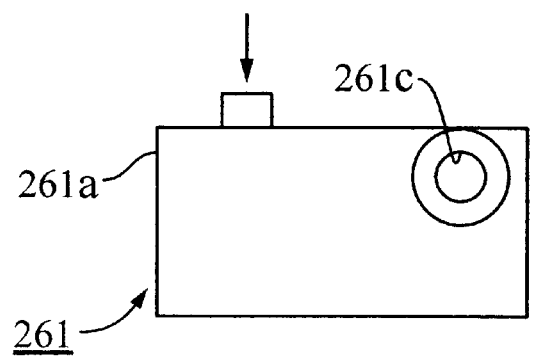
FIG. 4 is a plan view of FIG. 3.

Said humidifying/cooling apparatus 26 are constituted by a heat exchanger 261, a freezing unit 262, and a drainage valve 263. As illustrated in FIGS. 3 and 4, said heat exchanger 261 comprises a case 261a having an inlet and an outlet, both for processed gas, a cooling coil 261b contained within said case, and a metallic tube 261c connected to said outlet while positioned in contact with said cooling coil for guidance of processed gas occurring at the outlet's side.

The following is the description of said one embodiment in terms of its operative sequence.

(1) An article being sterilized is put into the sterilization chamber 11 and the door of said chamber is closed. The suction valve 22a and discharge valve 22b are closed against inroads of formalin gas into the formalin gas counteracting and deodorizing device 20 from said chamber, while the selector valves 31 and 32 are kept open so that the idle circuit 30 is ready for a prompt use.

(2) The sterilizer 10 is started up, and then, the temperature in the chamber is raised to 60° C. using the fan 16 and heater 15 for warming the interior of the chamber and 200 cc of formalin is made to vaporize to set the formalin gas concentration from 12% to 13%.

(3) The operation of the counteracting and deodorizing device 20 is started ten minutes before the end of the predetermined sterilization time of ninety minutes (at the end of sterilization, the formalin concentration is 3000 RPM and the humidity is 40%). The operation of the dehumidifying/cooling apparatus 26 is started ten minutes before the end of said time, and the operations of the fan 23 and preheater 24 are started five minutes before the end of said time, so that the gas is circulated along the idler circuit 30 and the decomposition-treat operation is stabilized (the gas is heated by the preheater 24 to 230° C.).

(4) When the predetermined sterilization time has passed and the sterilization work has come to end, the decomposition-treat operation is started in the sterilizing chamber. That is, the selector valves 31, 32 are closed to stop up the idler circuit 30, and with the suction and discharge valves 22a, 22b kept open, the formalin-containing air is heated by the preheater 24, counteracted and deodorized in the presence of catalyst, then dehumidified by the dehumidifying/cooling apparatus 26, then cooled to a normal temperature (20 to 35° C.), and returned to the sterilizing chamber.

(5) After performed for 30 minutes, the decomposition-treat operation in the chamber is stopped. The gas is circulated using the fan 16 of the chamber, then the counteractive is made vaporize (100 cc and the concentration of ammonia: 12 to 13%). With the suction and discharge valves 22a, 22b closed and the selector valves 31, 32 opened, the operation of the counteracting and deodorizing device 20 is stopped.

(6) Ten minutes before the end of the construction time (20 minutes), the counteracting and deodorizing device 20 (the dehumidifying/cooling apparatus 26) is started up. Then the operations of the fan 23 and preheater 24 are started five minutes before the end of said time, so that the gas is circulated in the idler circuit 30 and the operation of the decomposition-treat operation is stabilized (the gas is heated by the preheater 24 to 260° C.).

(7) When the counteraction time has passed and the counteraction work has come to end, the decomposition-treat operation is started in the sterilization chamber. With the selector valves 31, 32 closed to stop up the idler circuit 30, the suction valve 22a and discharge valve 22b are opened and the counteractive-containing air is heated by the preheater 24, counteracted and deodorized in the presence of catalyst, then dehumidified by the dehumidifying/cooling apparatus 26 and cooled to a normal temperature (20 to 35° C.), and returned to the chamber.

(8) After performed within the sterilization chamber for 20 minutes, the decomposition-treat operation is discontinued, and the operation of the sterilizer 10 is stopped (at the end of the operation, the formalin concentration is below 0.03 PPM, and the relative humidity is 10%). Then, the suction valve 22a and discharge valve 22b are closed, the selector valves 31, 32 are opened, and the operation of the counteracting and deodorizing device 20 is stopped.

As a result of such an operation, a concentration of under 0.03 PPM has been attained without discharging the sterilized formaldehyde gas from the sterilization chamber filled therewith. This is an epoch-making system which may avoid any environmental pollution (the treatment time is 30 to 60 minutes). In the heat exchanger 261 of the dehumidifying/cooling apparatus, a heated gas may be cooled very efficiently by getting in touch with the cooling coil 261b and the inside of the metallic tube 261c at the outlet's side as well. In particular, since the metallic tube 261c abuts on the cooling coil 261b, the heat of low-temperature medium carries well. This enables production of a compact device as a whole accordingly.

Figure 2:
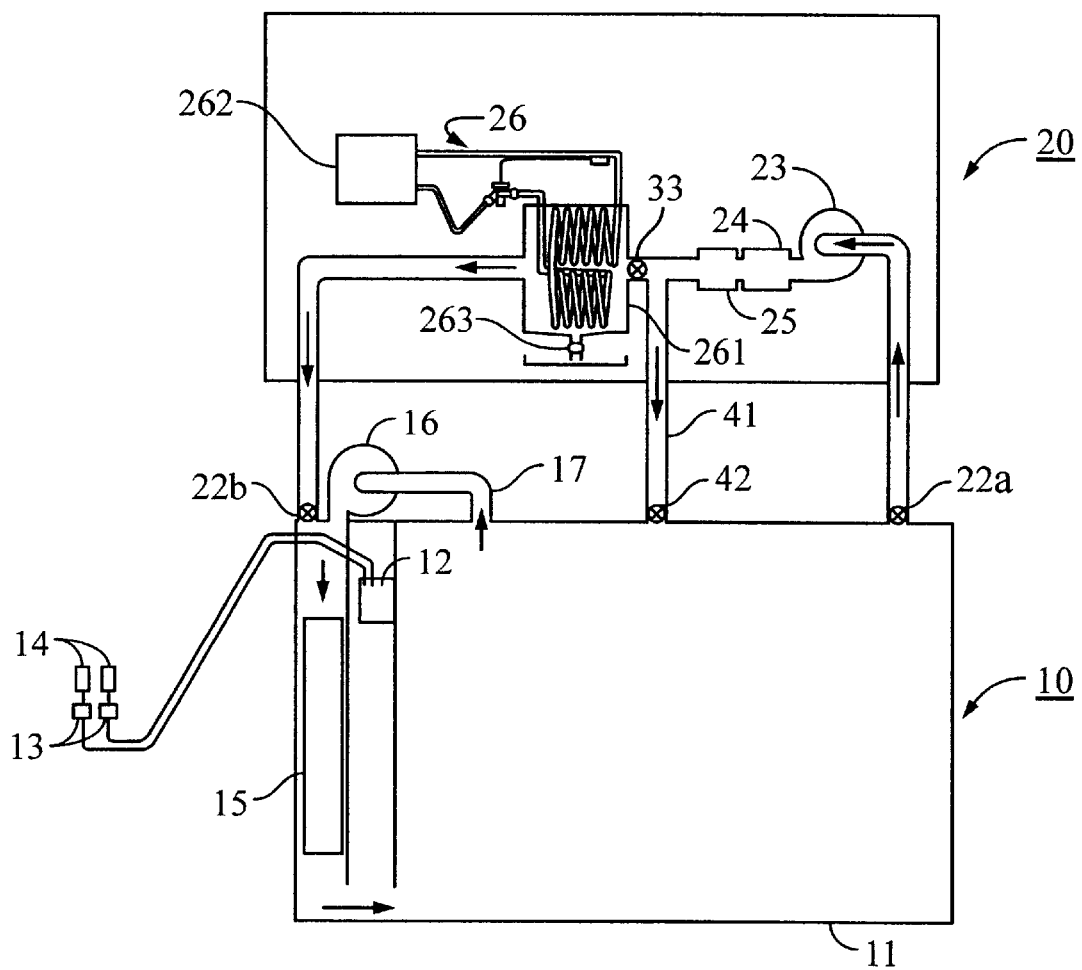
FIG. 2 is a system diagram of the other embodiment of the present invention.

FIG. 2 shows another embodiment, wherein a branch pipe 41 is disposed between the decomposition by oxidization means 25 and cooling means 26 in said main pipeline 21 to connect to the sterilization chamber 11 via a second discharge valve 42. The other members are the same as those in FIG. 1.

Next, the operational sequence in the other embodiment will be described.

(1) An article to be sterilized is introduced into the sterilizing chamber 11 and the door is closed. All the valves are closed so as to prevent the formalin from entering from the sterilization chamber into the counteracting and deodorizing device 20.

(2) The operation of the sterilizer 10 is started to raise the temperature within the chamber to 60° C. using the chamber warming fan 16 and the warming heater 15 before the antiseptic (200 cc, and formalin concentration: 12 to 13%) is vaporized.

(3) When the predetermined sterilization time (90 minutes) has passed and the sterilization is over, the operation of the counteracting and deodorizing device 20 is started in order to circulate the gas for idling along the branch pipe 41 for five minutes (the formalin concentration at the end of sterilizing operation: 3000 PPM, the humidity: 40%). The suction valve 22a and the second discharge valve 42b are opened and a third selector valve 33 is closed at the time when the sterilization is over, then, the operations of the dehumidifying/cooling apparatus 26, the fan 23, and preheater 24 are started, and the formalin-containing air is heated by the preheater to 230° C., and after counteracted and deodorized in the presence of catalyst, the air is returned to the sterilization chamber.

(4) The decomposition-treat operation within the sterilization chamber is started five minutes after the end of the sterilization. With the second discharge valve 42 closed and the third selector valve 33 and the first discharge valve 22b opened, the air remaining in the sterilization chamber after its return is counteracted and deodorized in the presence of catalyst, passed through the dehumidifying/cooling apparatus 26 for dehumidifying purpose, cooled to a normal temperature (20 to 35° C.), and returned to the sterilization chamber 11.

(5) The decomposition-treat operation within the chamber is stopped after it has been carried out for 30 minutes. Then, the counteractive (100 cc, and ammonia concentration: 12 to 13%) is vaporized. The heater of the preheater 24 is switched off, and five minutes after, the second valve 42 is opened and the third selector valve 33 and the first discharge valve 22b are closed, then the dehumidifying/cooling apparatus 26 is stopped (the operations of the counteracting and deodorizing device are stopped).

(6) Upon termination of the counteraction time, the operation of the counteracting and deodorizing device 20 is started in order to circulate the gas for idling along the branch pipe 41 for the next five minutes. At the end of the counteraction process, the suction valve 22a and the second discharge valve 42 are opened, and the third selector valve 33 is closed, the dehumidifying/cooling apparatus 26, fan 23, and preheater 24 are started, and the counteractive/formalin-containing air is heated by the preheater to 260° C., counteracted and deodorized in the presence of catalyst, and returned to the sterilization chamber 11.

(7) Five minutes after the end of the counteraction time, the decomposition-treat operation within the sterilization chamber 11 is started. With the second discharge valve 42 closed and the third selector valve 33 and the first discharge valve 22b opened, the counteraction and deodorization in the presence of catalyst takes place, and then, the air which has been returned to the inside of the sterilization chamber is passed through the dehumidifying/cooling apparatus 26 for dehumidification, cooled to a normal temperature (20 to 35° C.), and returned to the sterilization chamber 11.

(8) After performed for 20 minutes, the above-described decomposition-treat operation is stopped, and the operation of the sterilizer 10 is stopped (formalin concentration at the end of the operation: below 0.03 PPM) (the relative humidity at the end of the operation: 10%). The heater of the preheater 24 is switched off, the second discharge valve 42 is opened five minutes after, and the third selector valve 33 and the first discharge valve 22b are closed, then the dehumidifying/cooling apparatus 26 is stopped (discontinuation of the operation of counteracting and deodorizing device).

The functions of the main members in said arrangement are as follows. The preheater raises the temperature to 230 to 260° C. before hand in order to facilitate the reaction in the presence of catalyst. The catalyst aids decomposition by oxidization of antiseptic gas (in case of formalin, the concentration is reduced from 3000 RPM to under 0.03 PPM). The dehumidifying/cooling apparatus serves to remove moisture in the air (the humidity within the sterilization chamber is reduced from 60% to 5%) and to return the temperature to a normal one. The suction valve acts to prevent gas inside of the sterilization chamber from etching into the decomposition treatment system. The discharge valve acts to prevent gas inside the sterilization chamber from entering into the decomposition treatment system. The selector valve acts to selectively control the decomposition-treat operation in the sterilization chamber.

The specification of the main members used in the experiments is as follows.

Referring to the preheater, nichrome wires are used as a heat source, and air is sent by an electric blower (capacity: 5 KW for heater, and 0.1 KW for blower). A honeycomb-formed structure made of platinum or rhodium is used as catalyst. The dehumidifying/cooling apparatus is constituted by a refrigerating machine using refrigerant condenser unit and a heat exchanger, wherein a heated gas is passed through the heat exchanger to cool the gas by the use of refrigerant (fluorocarbon 22) and remove moisture from it. The dimensions (mm) are as follows. Case: 500 (width)×250 (length)×700 (height); refrigerant pipe: 15 (diameter)×15 m (length); coil: 150 (diameter); metallic tube: 65 (diameter)×600 (length). The suction valve is of a two-way type (electrically-powered); discharge valve is of a two-way type (electrically-powered); selector valve is of a two-way type (electrically-powered). Referring to the measurement method, the detection of formalin concentration was carried using the detecting pipe system (Gastec), and the humidity was measured by the humidity detectors RHS-302 and SRF-106 (Yamatake-Honeywell).

Additionally, a small amount of power is sufficient as a whole for cooling purpose if an air-cooled cooler is provided in front of said dehumidifying/cooling apparatus.

The present invention includes variety of variations without deviating from the spirit and scope of the claims, and is not limited to such examples and embodiments as described above.

INDUSTRIAL FIELD OF APPLICATION

The present invention is applicable to the process and device for counteracting and deodorizing formalin gas.

What is claimed is:

1. A process for counteracting and deodorizing formalin gas which comprises:

connecting to a sterilization chamber a formalin gas counteracting and deodorizing device which includes a main pipeline having an inlet for formalin gas at one end thereof and an outlet for processed gas at the other; a fan connected to said inlet side midway in said main pipeline; a preheater means; an oxidization means for decomposing; and a cooling means all ranging in this order from said fan to said outlet to connect to each other; and a bypass pipeline provided to cover a section extending from the fan of said main pipeline to the cooling means, performing sterilization by means of said sterilization chamber for predetermined period of time, circulating the gas between said main pipeline and said bypass pipeline for a predetermined period of time by said formalin gas counteracting and deodorizing device just before the end of said sterilization process, then circulating the gas between the sterilization chamber and the main pipeline for counteracting said formalin gas, introducing a counteractive into the sterilization chamber, and then administering the same treatment as done in said formalin gas.

2. A process for counteracting and deodorizing formalin gas which comprises:

connecting to a sterilization chamber a formalin gas counteracting and deodorizing device which includes a main pipeline having an inlet for formalin gas at one end thereof and an outlet for processed gas at the other; a fan connected to said inlet side midway in said main pipeline; a preheater; an oxidization means for decomposing; a cooling means all ranging in this order from said fan to said outlet to connect to each other; and a branch pipe provided between the oxidization means of said main pipeline and the cooling means;

performing sterilization by the use of said sterilization chamber for predetermined period of time, circulating the gas between said pipeline, said branch pipe and said sterilization chamber for a predetermined period of time by the use of said formalin gas counteracting and deodorizing device after the end of said sterilization course, then circulating the gas between the sterilization chamber and the main pipeline for counteracting said formalin gas with said branch pipe closed, then introducing a counteractive into the sterilization chamber, and making the same treatment as done in the case of said formalin gas.

3. A device for counteracting and deodorizing formalin gas which comprises:

a main pipeline having an inlet for formalin gas at one end thereof and an outlet for processed gas at the other, a fan connected to said inlet side midway in said main pipeline, a preheater, an oxidization means for decomposing, and a cooling means all ranging in this order from said fan to said outlet to connect to each other, and a bypass pipeline provided to cover a section extending from the fan of said main pipeline to the cooling means.

4. A device for counteracting and deodorizing formalin gas which comprises:

a main pipeline having an inlet for formalin gas at one end thereof and an outlet for processed gas at the other, a fan connected to said inlet side midway in said main pipeline, a preheater, an oxidization means for decomposing, a cooling means all ranging in this order from said fan to said outlet to connect to each other, and a branch pipe provided between the oxidization means for decomposing of said main pipeline and the cooling means.

5. The process for counteracting and deodorizing formalin gas according to any one of above claims 1 or 2 wherein said cooling means includes:

a case having an inlet and outlet for processed gas, a cooling coil contained in said case, and a metallic tube connected to said outlet while remaining in contact with said coil so as to direct the processed gas at the outlet.

6. The process for counteracting and deodorizing formalin gas according to claim 5 wherein said sterilization chamber is connected to said inlet and outlet for said processed gas.

* * * * *